(12) United States Patent
Venturini (10) Patent No.: US 12,161,367 B2
(45) Date of Patent: Dec. 10, 2024

(54) DEVICE FOR THE ANGULAR CORRECTION OF A LOWER LIMB IN PEDIATRIC PATIENTS

(71) Applicant: ORTHOFIX S.R.L., Bussolengo (IT)

(72) Inventor: Daniele Venturini, Povegliano Veronese (IT)

(73) Assignee: Orthofix S.R.L., Bussolengo (IT)

( * ) Notice: Subject to any disclaimer, the term of this patent is extended or adjusted under 35 U.S.C. 154(b) by 686 days.

(21) Appl. No.: 17/435,933

(22) PCT Filed: Mar. 4, 2020

(86) PCT No.: PCT/EP2020/055703
§ 371 (c)(1),
(2) Date: Sep. 2, 2021

(87) PCT Pub. No.: WO2020/178343
PCT Pub. Date: Sep. 10, 2020

(65) Prior Publication Data
US 2022/0142676 A1 May 12, 2022

(30) Foreign Application Priority Data
Mar. 6, 2019 (IT) .................. 102019000003283

(51) Int. Cl.
*A61B 17/66* (2006.01)
*A61B 17/62* (2006.01)
(52) U.S. Cl.
CPC .............. *A61B 17/66* (2013.01); *A61B 17/62* (2013.01)

(58) Field of Classification Search
CPC ................................ A61B 17/62; A61B 17/66
See application file for complete search history.

(56) References Cited

U.S. PATENT DOCUMENTS 5,102,411 A * 4/1992 Hotchkiss .............. A61B 17/62
606/56
5,108,393 A * 4/1992 Ruffa ........................ A61F 5/04
606/56

(Continued)

FOREIGN PATENT DOCUMENTS

DE        8304490 U1    4/1986
DE    102015121357 A1   6/2017

(Continued)

OTHER PUBLICATIONS

International Searching Authority/European Patent Office, "International Search Report," for PCT/EP2018/086088, mailed Jun. 23, 2020, 5 pages.

(Continued)

*Primary Examiner* — Tessa M Matthews
(74) *Attorney, Agent, or Firm* — Haynes and Boone, LLP (57) ABSTRACT

Device for the angular correction of a lower limb in pediatric patients, comprising: a first fixator body and a second fixator body which are both shaped like a ring or ring portion and can be placed around a lower limb and fixed to two bone sites of said lower limb straddling a growth cartilage, said first fixator body and said second fixator body being constrained together slidably along their annular extension; and adjusting means suitable for allowing relative sliding of said first fixator body with respect to said second fixator body.

7 Claims, 15 Drawing Sheets

(56) References Cited

U.S. PATENT DOCUMENTS

| | | | | |
|---|---|---|---|---|
| 5,372,597 | A | * 12/1994 | Hotchkiss | A61B 17/6425 |
| | | | | 606/56 |
| 5,537,704 | A | * 7/1996 | Dinkler | A61B 90/14 |
| | | | | 5/643 |
| 6,860,883 | B2 | * 3/2005 | Janowski | A61B 17/645 |
| | | | | 606/56 |
| 2010/0234844 | A1 | 9/2010 | Edelhauser et al. | |

FOREIGN PATENT DOCUMENTS

| | | |
|---|---|---|
| EP | 3127498 A1 | 2/2017 |
| SU | 728849 A1 | 4/1980 |
| WO | 96/34585 A1 | 11/1996 |
| WO | 03/086211 A1 | 10/2003 |

OTHER PUBLICATIONS

International Searching Authority/European Patent Office, "Notification of Transmittal of the International Preliminary Report on Patentability," for PCT/EP2020/055703, mailed May 25, 2021, 16 pages.

* cited by examiner

DEVICE FOR THE ANGULAR CORRECTION OF A LOWER LIMB IN PEDIATRIC PATIENTS

FIELD OF APPLICATION

The present invention relates to a device for the angular correction of a lower limb in pediatric patients.

The invention therefore has a useful application in the sector of orthopedics, in particular corrective orthopedics.

PRIOR ART

In orthopedics it is known there exists the need for rotational or angular correction of the lower limb, intended to correct defects which may be congenital in nature or which may have arisen following injury or incorrect healing of fractures.

In the specific case of congenital defects or in any case defects which have arisen at an early age there currently exist three treatment techniques which make use of the growth of the cartilage.

A first technique employed is of the intraoperative type. During this treatment an intraoperative angular correction is combined with an internal—plate or nail—device for subsequent stabilization or elongation. Such an approach, however, is anatomically possible—without risk for the patient—only for small angles of correction; in order to obtain further angular correction a second operation is required.

A second technique, which is nowadays widely used, involves osteotomy of the bone and subsequent manipulation of the callus by means of an external fixation system, typically of the circular type. This approach, which is performed at the end of or towards the end of the growth, requires however long treatment times (the callus is allowed to form, the bone callus is manipulated using the fixator and then consolidation of the callus is allowed to take place); moreover, it may result in pain for the patient owing to the osteotomy.

A third technique, which has been recently tested and is described for example in the U.S. Pat. No. 10,076,375, uses internal devices for guiding the growth cartilage and correction of the angular error. This solution however also has a number of drawbacks: the need for two operations, the impossibility of correcting any deviation from the predefined plane or torsional angle and the risk of producing secondary angular deviations where the growth cartilage is not uniformly guided.

Documents WO 96/34585 A1, WO 03/086211 A1, EP 3 127 498 A1, SU 728 849 A1, DE 10 2015 121 357 A1 and US 2010/0234844 A1 disclose external fixators according to the prior art.

The technical problem underlying the present invention is that of proposing a device for the angular correction of the lower limb, which is innovative in nature, i.e. which allows a novel orthopedic approach to angular correction without at least some of the aforementioned drawbacks of the methods which are currently used.

SUMMARY OF THE INVENTION

The idea for a solution forming the basis of the present invention is that of proposing a device which guides indirectly the growth cartilage into its correct anatomical configuration, namely by forcing the relative twisting of the bone portions above and below the growth cartilage.

The aforementioned technical problem is therefore solved by a device for angular correction of a lower limb in pediatric patients, comprising:

a first fixator body and a second fixator body which are both shaped like a ring or ring portion and can be placed around a lower limb and can be fixed to two bone sites of said lower limb straddling a growth cartilage, said first fixator body and said second fixator body being constrained together slidably along their annular extension; and adjusting means suitable for allowing relative sliding of said first fixator body with respect to said second fixator body.

The first fixator body and the second fixator body respectively comprise a first attachment base and a second attachment base.

First fixation means, for fixing the first fixator body to the first bone site, are provided directly at the first attachment basis.

Second fixation means, for fixing the second fixator body to the second bone site, are provided directly at the second attachment basis.

Thanks to this arrangement, the first and the second bone sites are both in the vicinity of the growth cartilage of the lower limb.

Owing to their configuration in the form of a ring or ring portion the two fixator bodies may be applied so that they surround the lower limb of the patient, for example in the region of the tibia. The possibility of relative sliding of the bodies along their annular extension therefore allows a rotation about an internal axis of the two rings, namely along the longitudinal axis of the bone, said result not being able to be achieved when the two bodies are constrained by means of a hinge.

The adjusting means, which may advantageously comprise a micrometric screw, therefore allow a gradual correction of the relative position of the two fixator bodies, thus forcing the bone portions above and below the growth cartilage and favoring ultimately the correction of the bone defect.

As mentioned above, the fixator bodies may be configured in the form of both a complete ring and a ring portion, namely an arc of a circle. When the device is applied in the region of the knee, this second configuration has the opening positioned at the rear, so that the movement is not hindered and the ergonomics of the device is improved.

The first fixation means and the second fixation means can be a fixator ring or half-ring and/or screw connectors.

There therefore exists the possibility of engagement using circular rings of the known type or screw clamps, depending on the means chosen by the surgeon to connect together the part below the growth cartilage and the part above it.

The adjusting means may advantageously comprise an operating member constrained to said first fixator body, said operating member engaging with a toothing integral with said second fixator body.

Said toothing is preferably formed on the outside of a cylindrical collar of said second fixator body.

The operating member is preferably a worm screw extending in a tangential direction with respect to said collar of the second fixator body.

This worm screw may be advantageously housed inside an enlarged base of the second fixator body, for example the same base which has the holes for coupling to a fixator ring and/or a screw connector.

Preferably, the first fixator body comprises at least one circular shaped guide piece, said at least one guide piece being slidably constrained to the collar by a flange coupled to said collar.

In particular, said at least one guide piece may be placed over said collar along a relative rotation axis of the two fixator bodies; said flange may be a cylindrical plate which is coupled internally to the collar and which radially contains the at least one guide piece, preventing relative misalignment of the two fixator bodies.

Preferably, said flange is coupled to said collar by means of fixing screws or other reversible fixing system known in the sector, so as to allow easy assembly or disassembly of the elements.

In one embodiment, the guide pieces may be two in number, planar-shaped and parallel to each other, said collar being inserted between said two guide pieces.

In an alternative embodiment, the guide piece may be one in number, and said flange may comprise a horizontal flap which surrounds and contains the said guide piece.

By means of the device described above it is possible to provide a method for angular correction of a lower limb in pediatric patients, comprising the steps of:
fixing a first fixator body and a second fixator body onto two portions of the bone of a lower limb to be corrected, on the two sides above and below the growth cartilage;
performing a gradual de-rotation of the bone, modifying the relative angular position of the two fixator bodies.

Forcing of the growth cartilage is performed by means of bone tools which may be wires or screws of varying sizes depending on the dimensions of the bone to be treated.

Perfect control during the correction is performed by means of a micrometric screw which is moved once or twice a day.

The time for which the device remains on the patient is limited to the time needed for correction.

Removal of the device may be performed on an outpatient basis, as occurs nowadays for the removal of external fixation systems.

The degree of daily torsional correction is indicated by the doctor depending on the various biological parameters of the patient.

Further characteristic features and advantages will emerge more clearly from the detailed description provided hereinbelow of preferred, but not exclusive embodiments of the present invention, with reference to the attached figures, provided by way of a non-limiting example.

DETAILED DESCRIPTION

Figure 1:
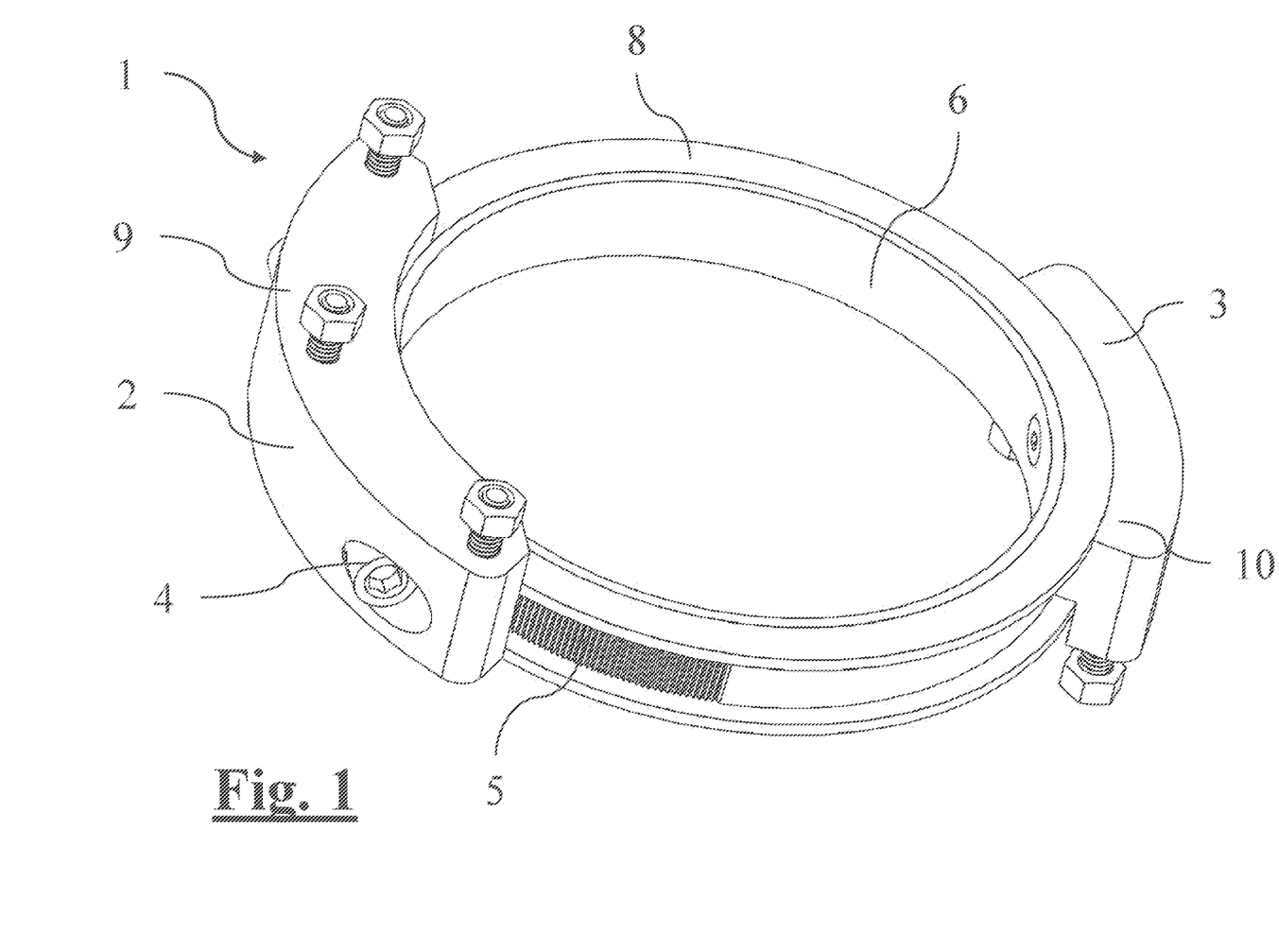
FIG. 1 shows a perspective view of a first embodiment of the device according to the present invention.
Figure 2:
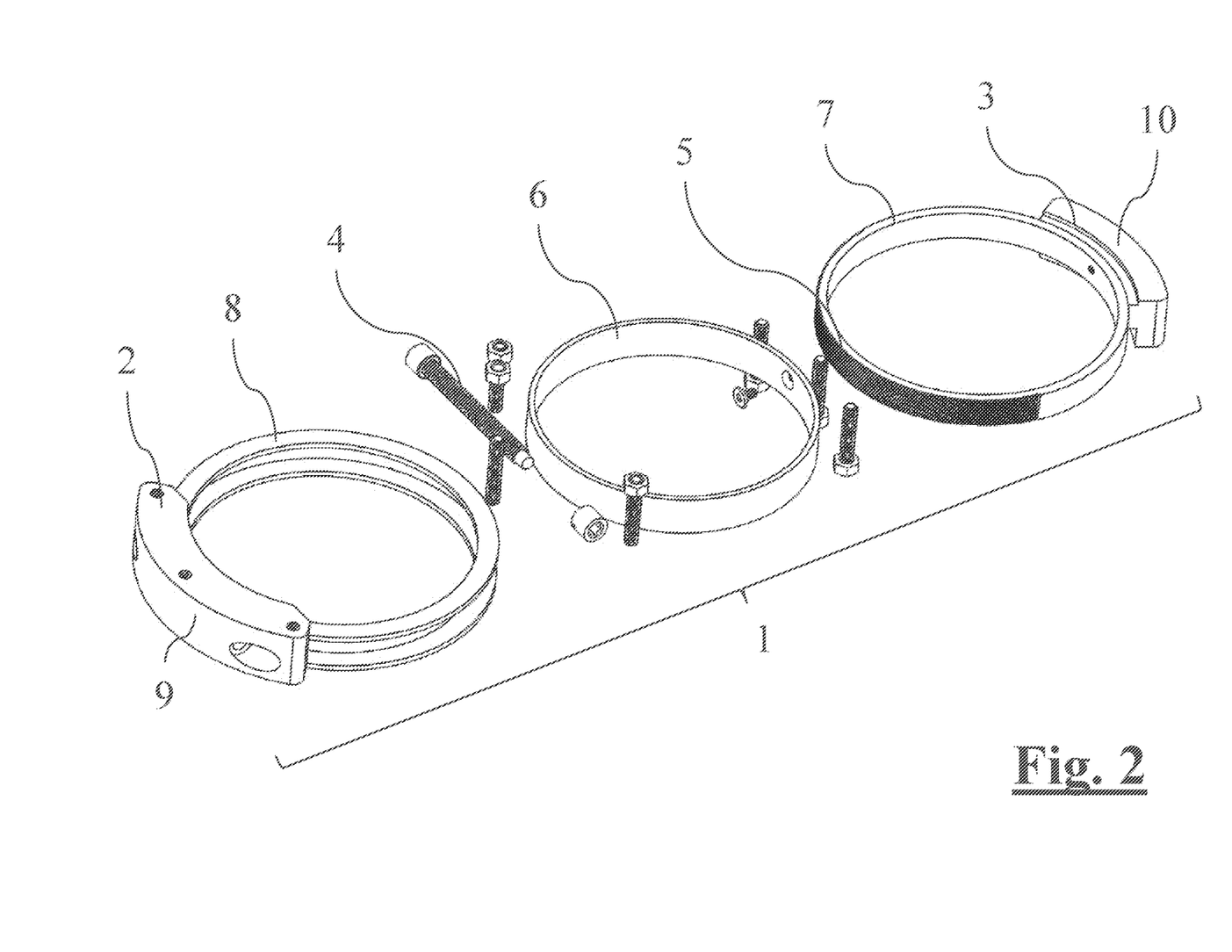
FIG. 2 shows an exploded view of the device according to FIG. 1.
Figure 3:
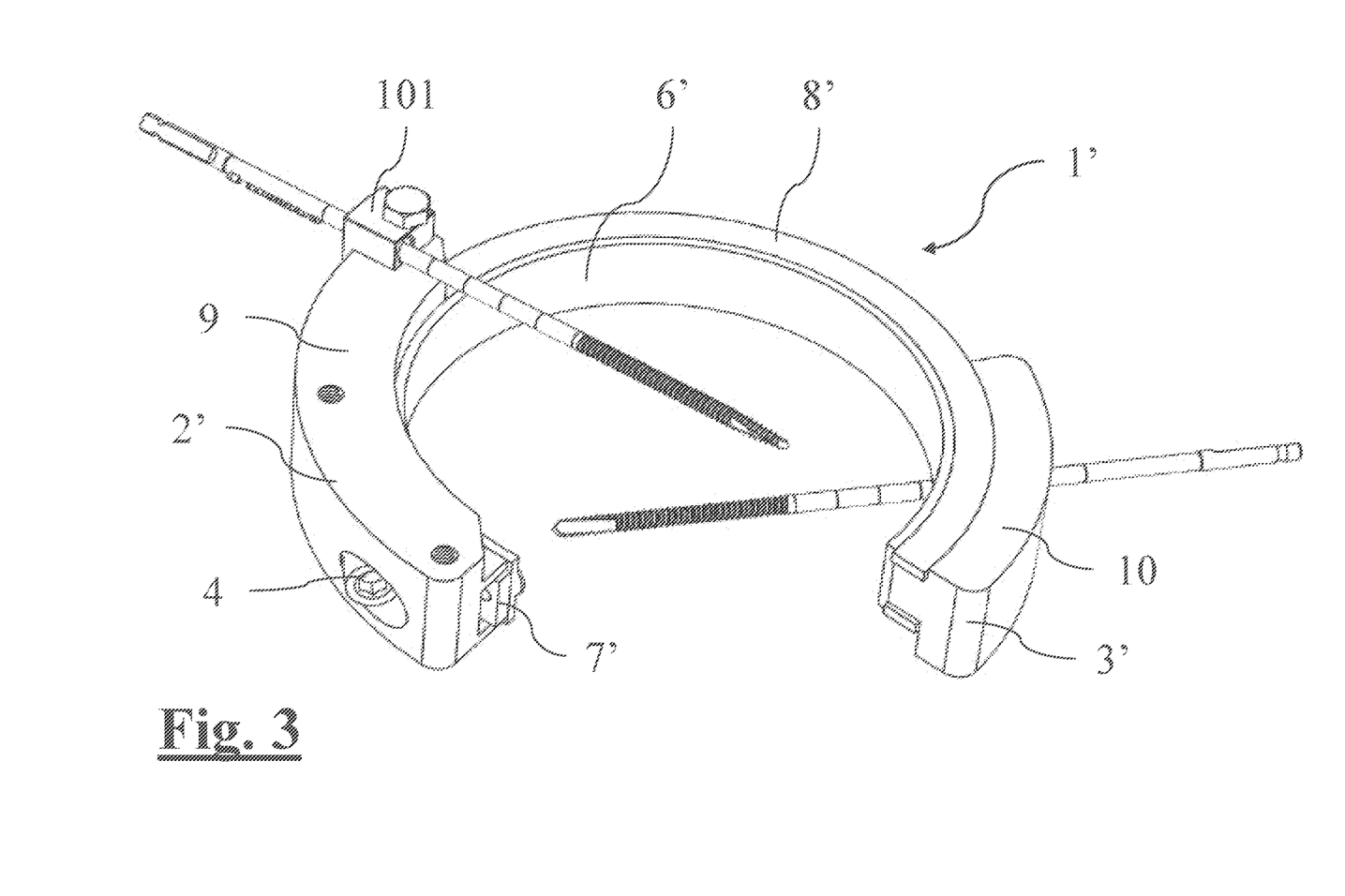
FIG. 3 shows a perspective view of a second embodiment of the device according to the present invention, coupled with endosseous screws.
Figure 4:
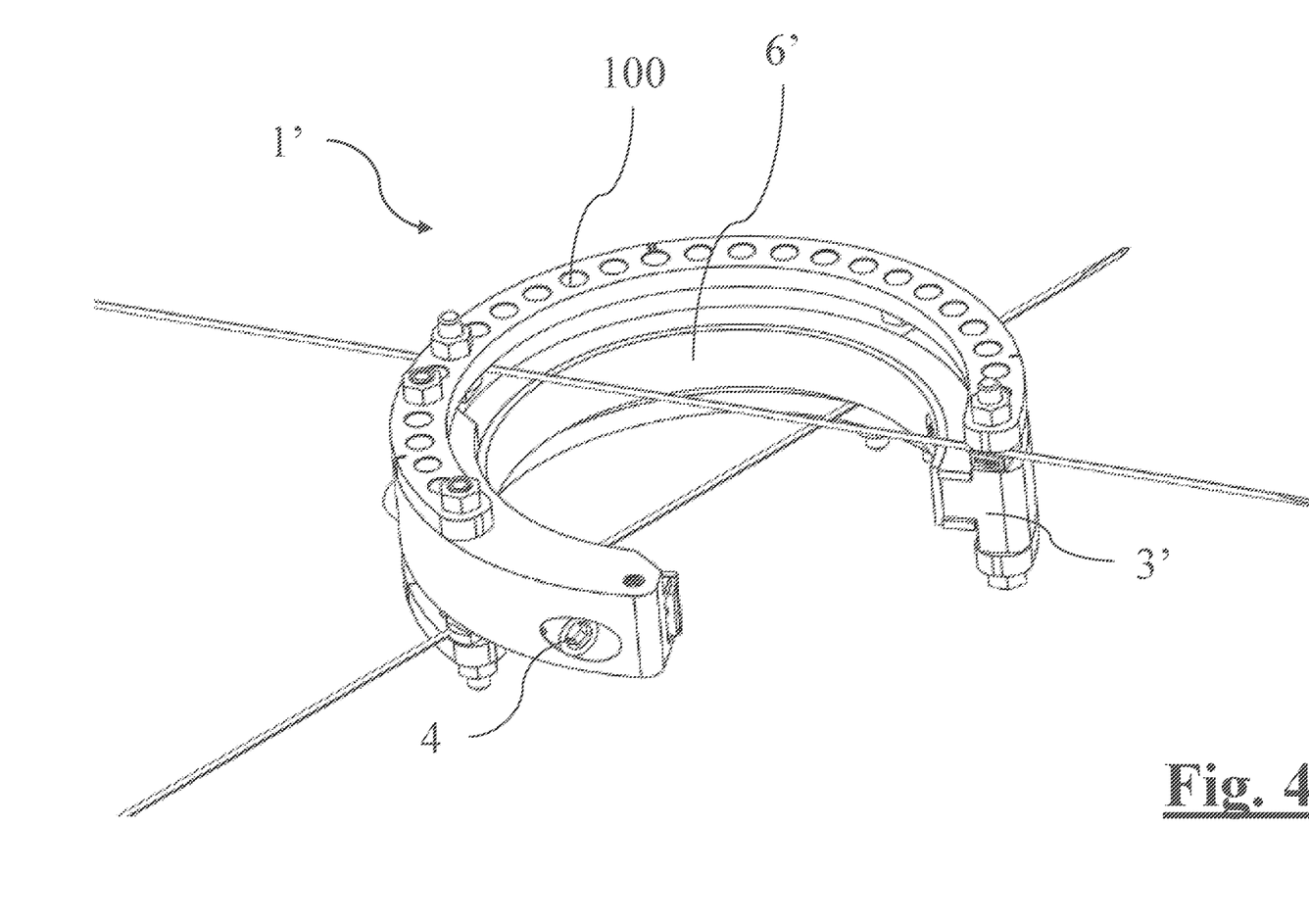
FIG. 4 shows a perspective view of the device according to FIG. 3 coupled with fixator rings and Kirschner wires.
Figure 5:
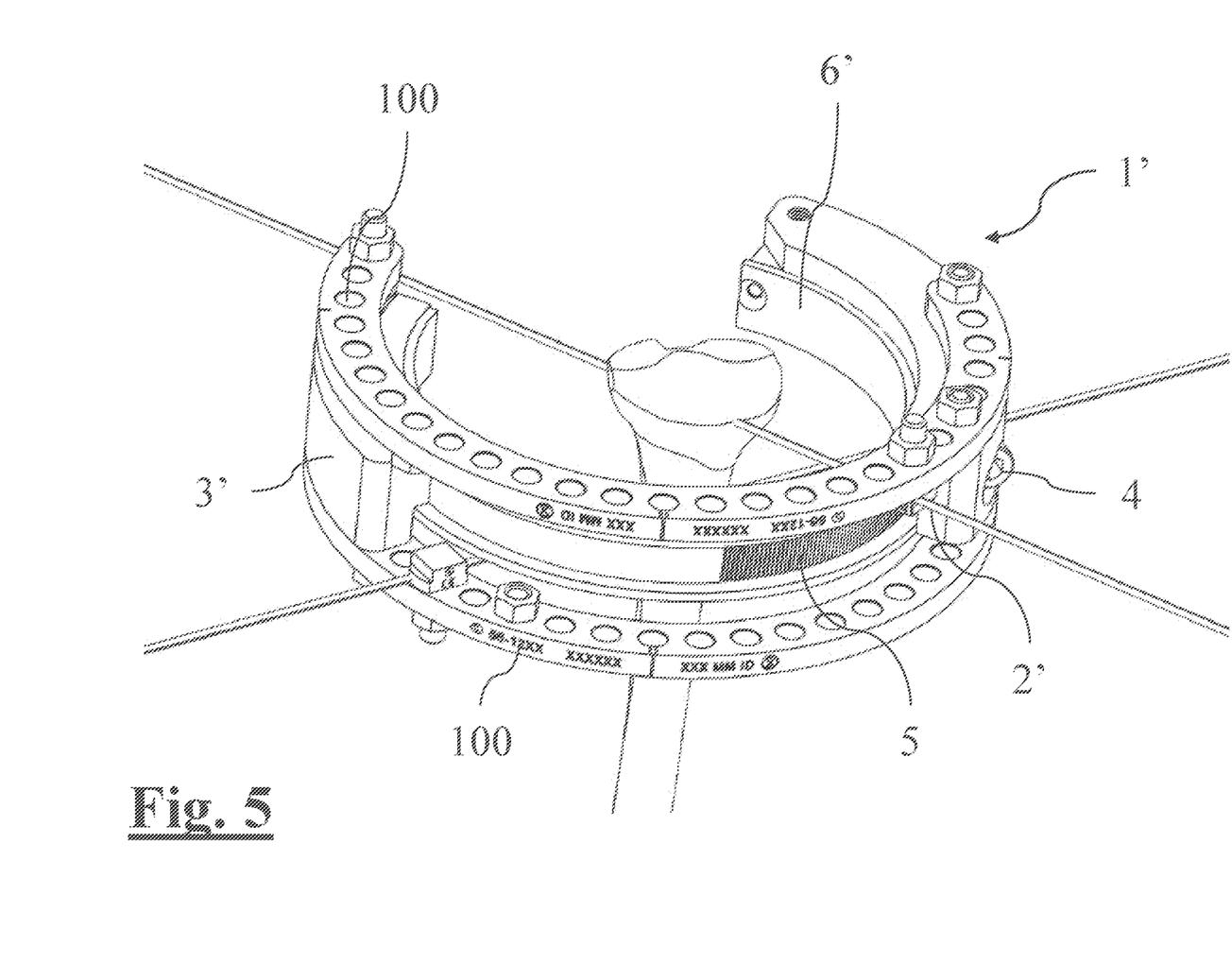
FIG. 5 shows a perspective view of the device according to FIG. 3 coupled with rings and Kirschner wires in a bone site of a patient.
Figure 6:
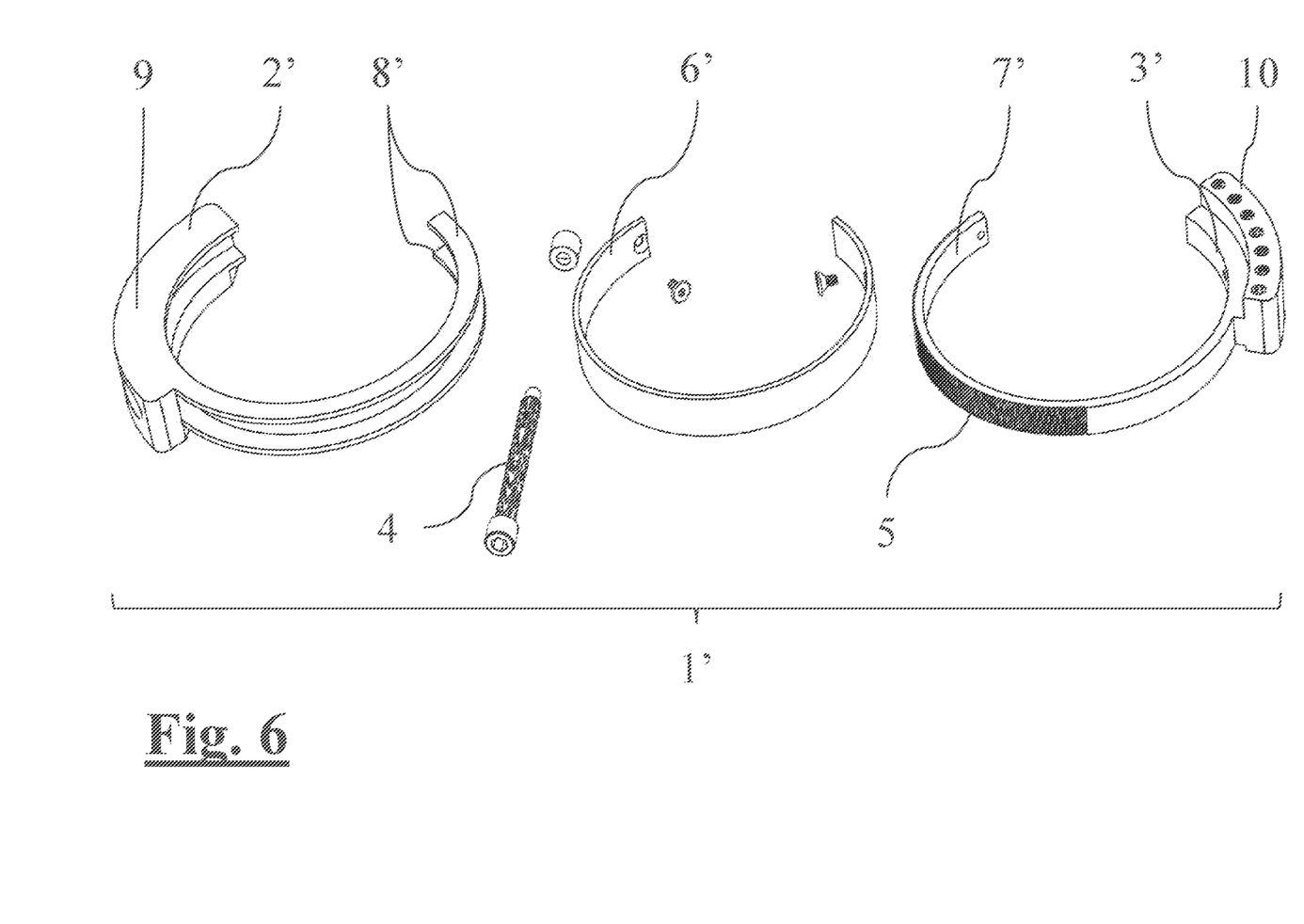
FIG. 6 shows an exploded view of the device according to FIG. 3.
Figure 7:
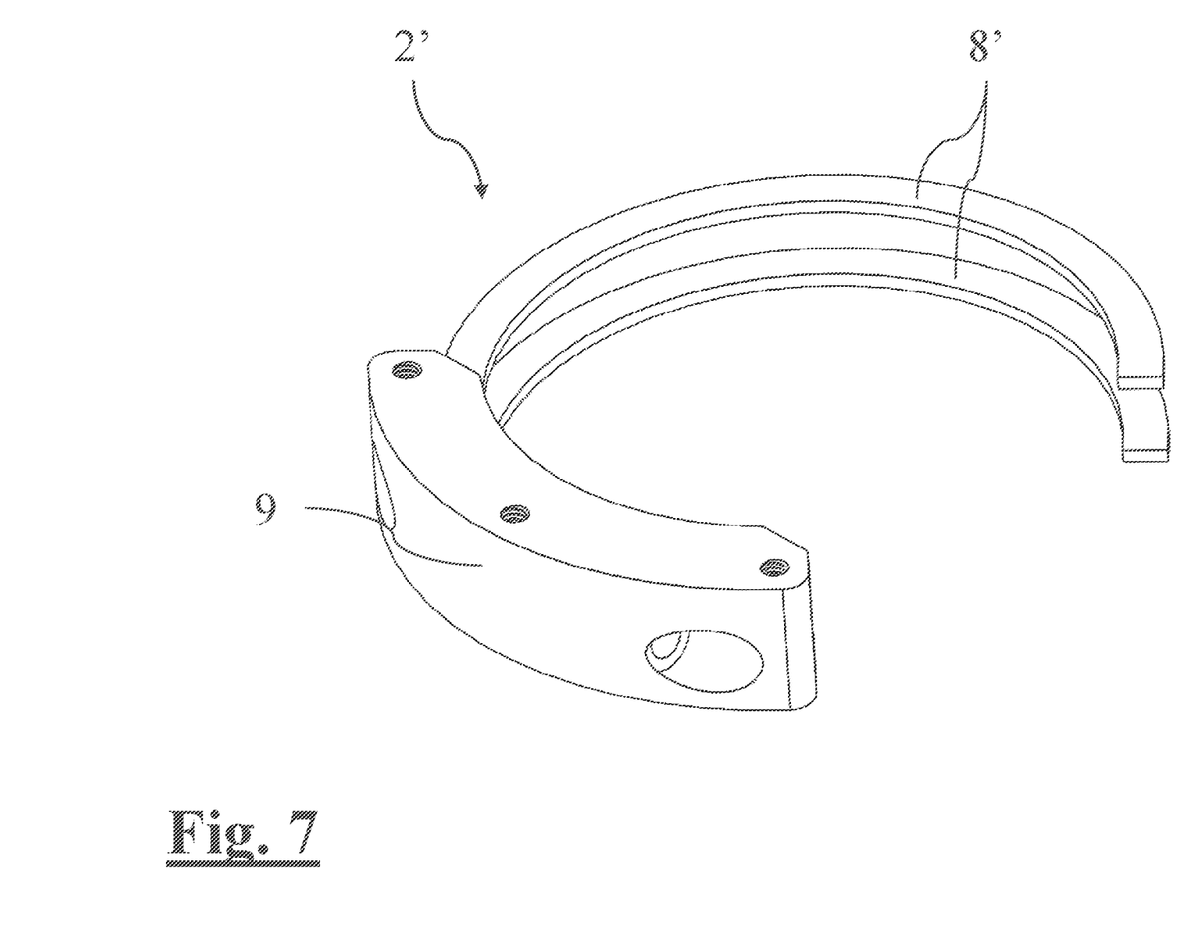
FIG. 7 shows a perspective view of a first element—referred to below as "first fixator body"—of the device according to FIG. 3.
Figure 8:
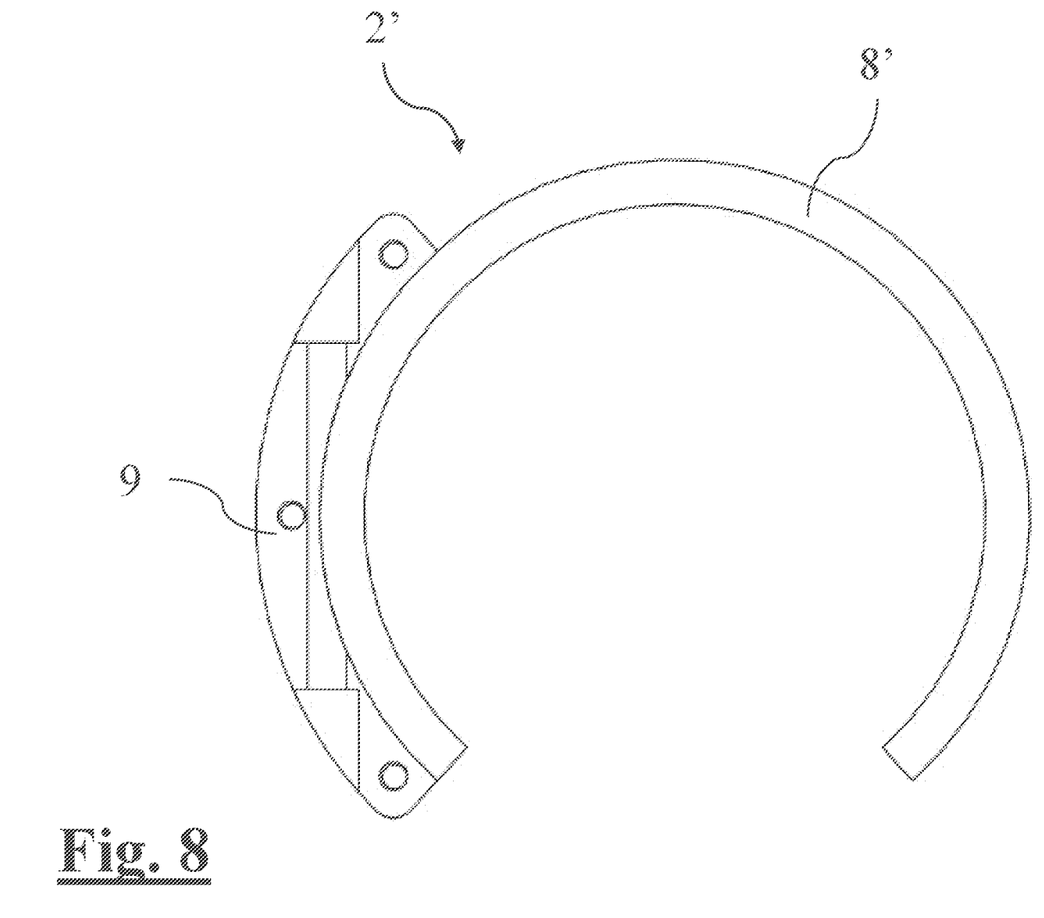
FIG. 8 shows a sectioned view from above of the first fixator body according to FIG. 1.
Figure 9:
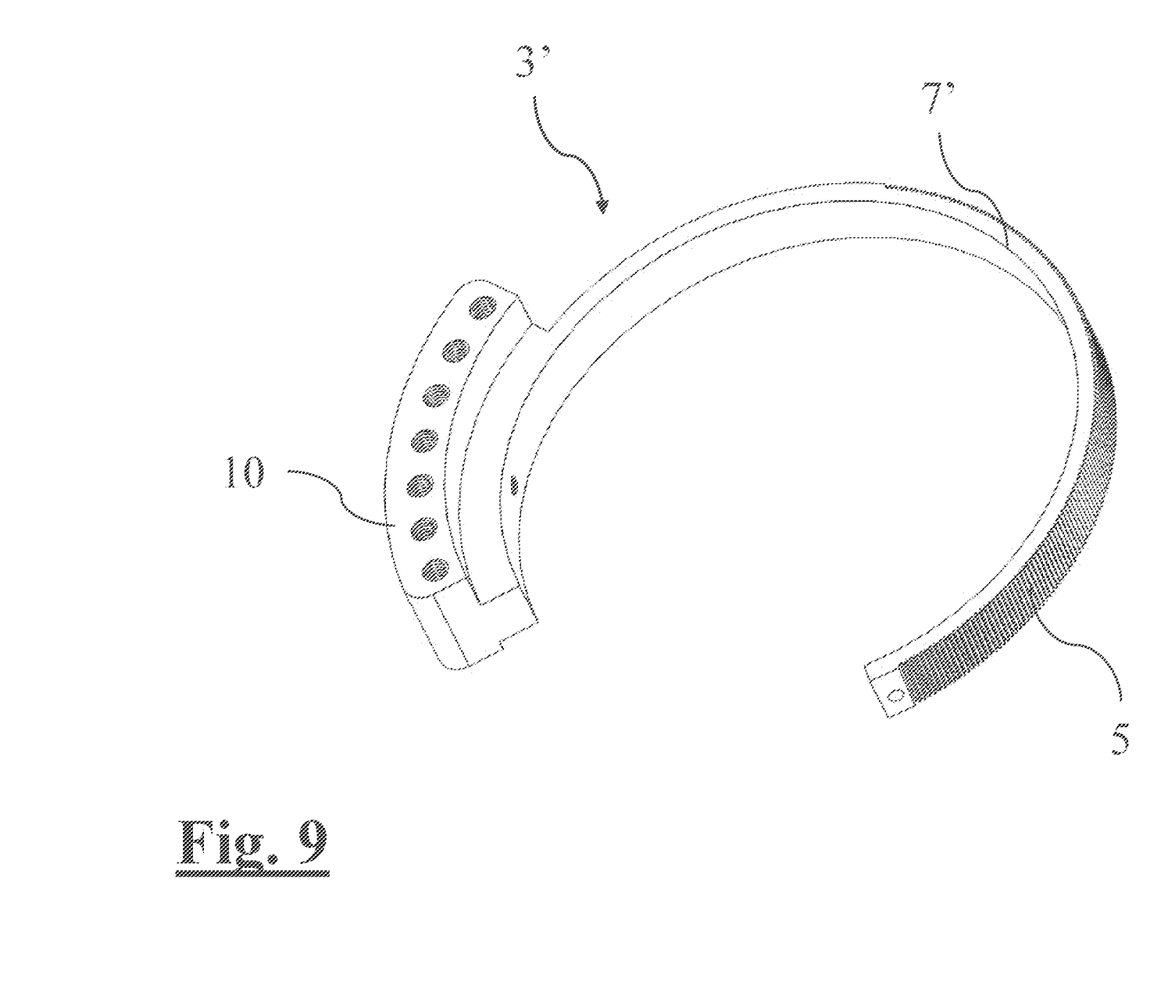
FIG. 9 shows a perspective view of a second element—referred to below as "second fixator body"—of the device according to FIG. 3.
Figure 10:
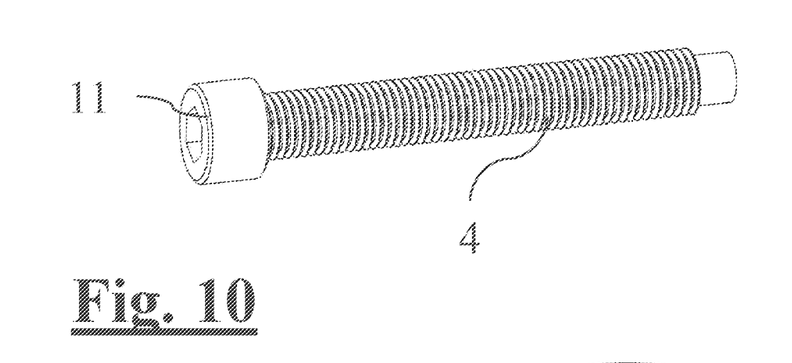
FIG. 10 shows a perspective view of the operating screw of the device according to FIG. 3.
Figure 11:
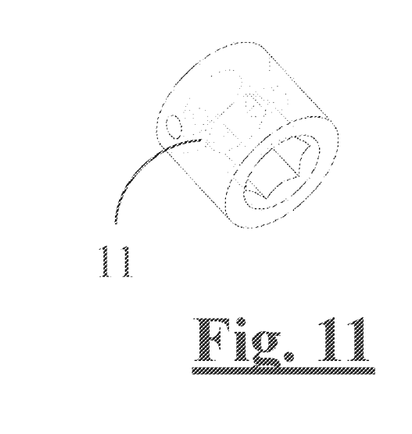
FIG. 11 shows a perspective view of a nut for closing the operating screw according to FIG. 10.
Figure 12:
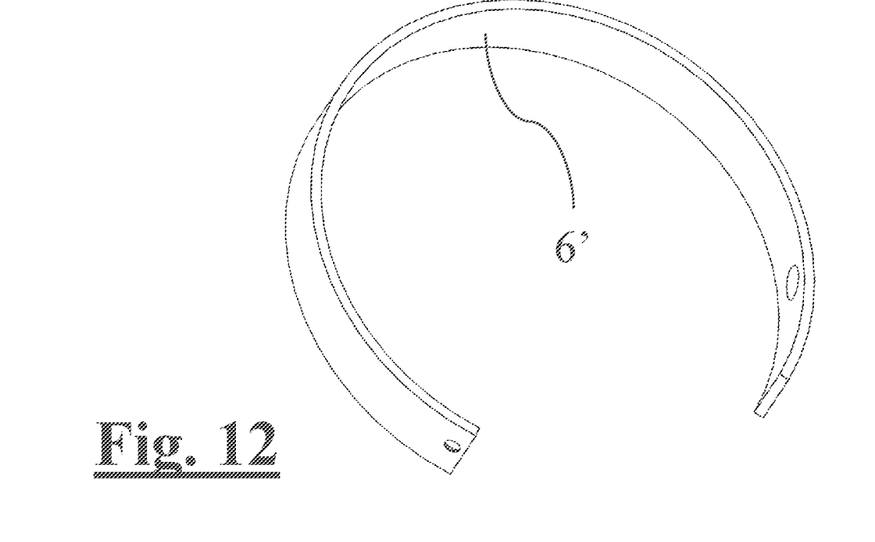
FIG. 12 shows a perspective view of a further element—referred to below as "flange"—of the device according to FIG. 3.
Figure 13:
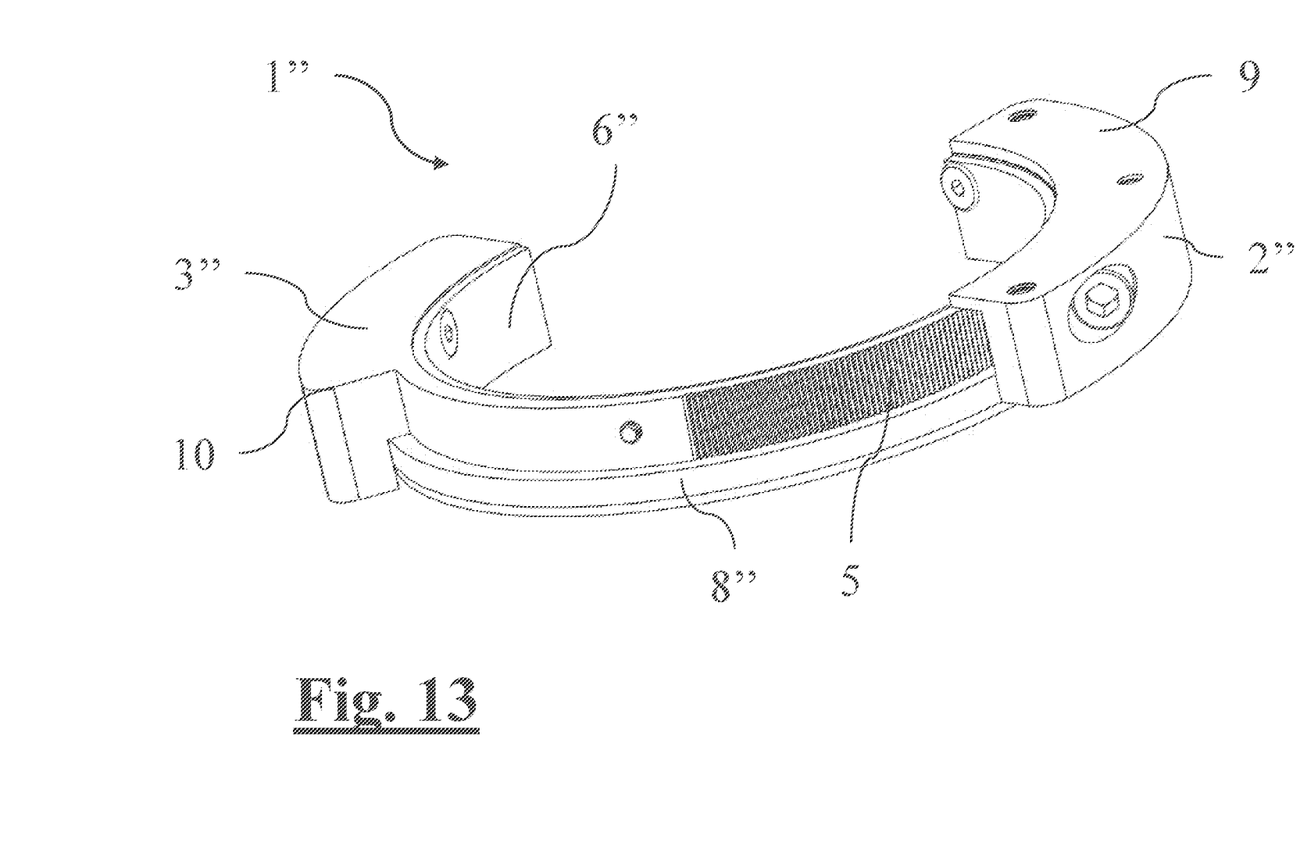
FIG. 13 shows a perspective view of a third embodiment of the device according to the present invention.
Figure 14:
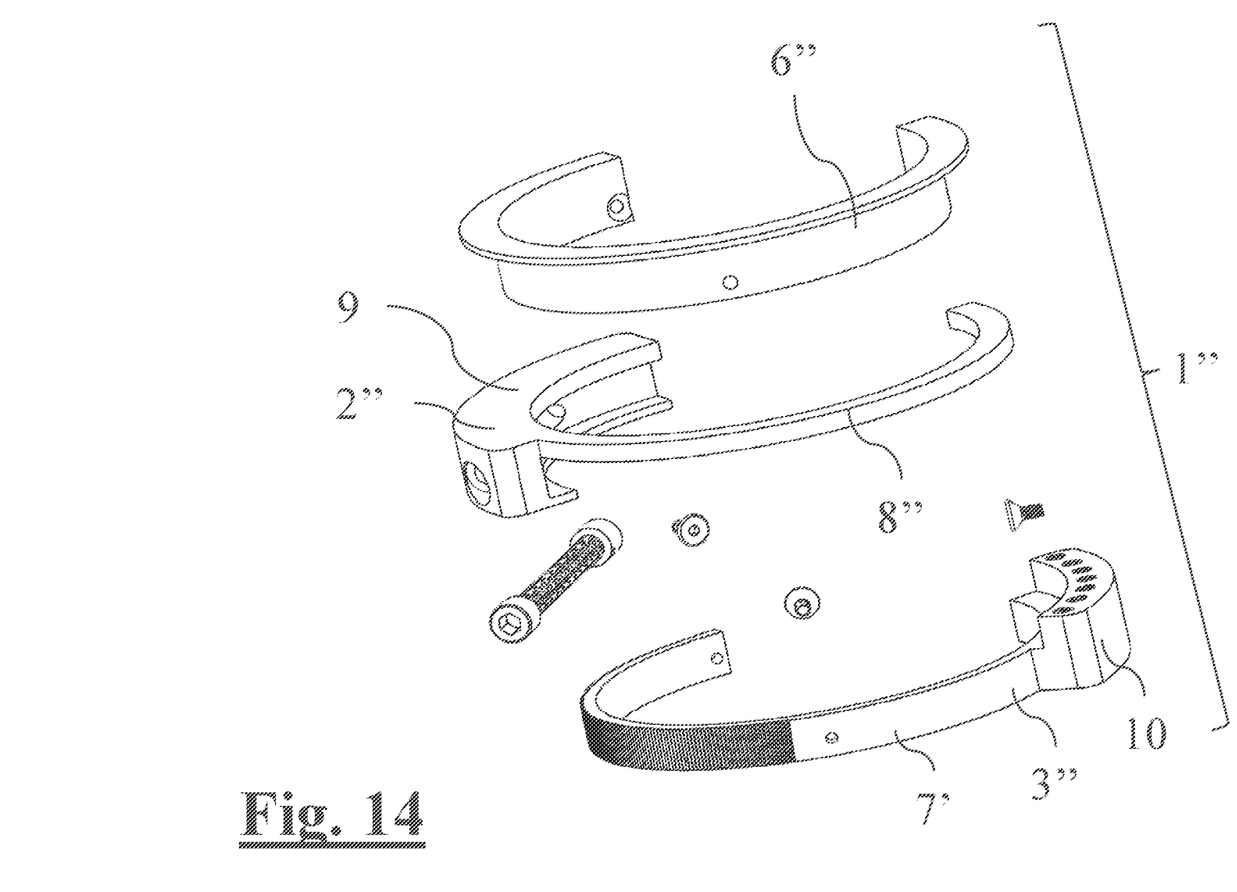
FIG. 14 shows an exploded view of the device shown in FIG. 13.
Figure 15:
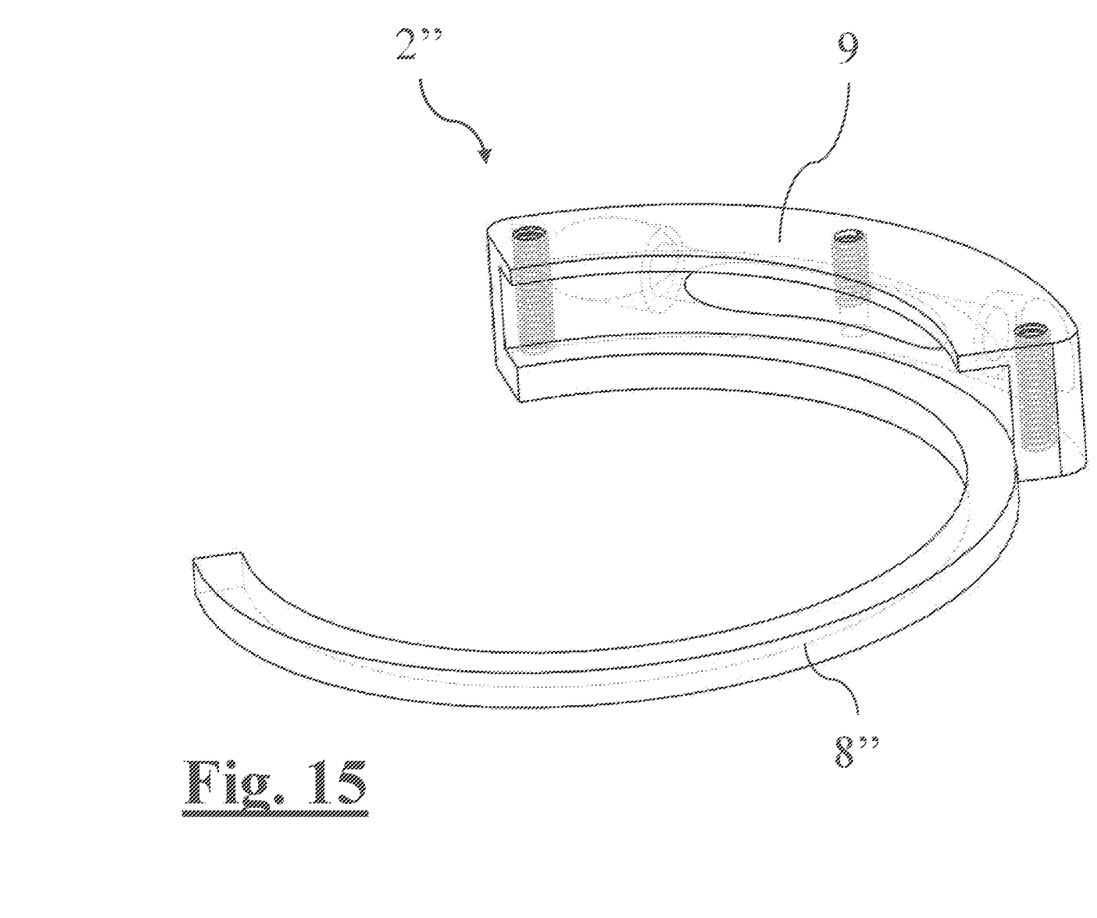
FIG. 15 shows a perspective view of a first element—referred to below as "first fixator body"—of the device according to FIG. 13.
Figure 16:
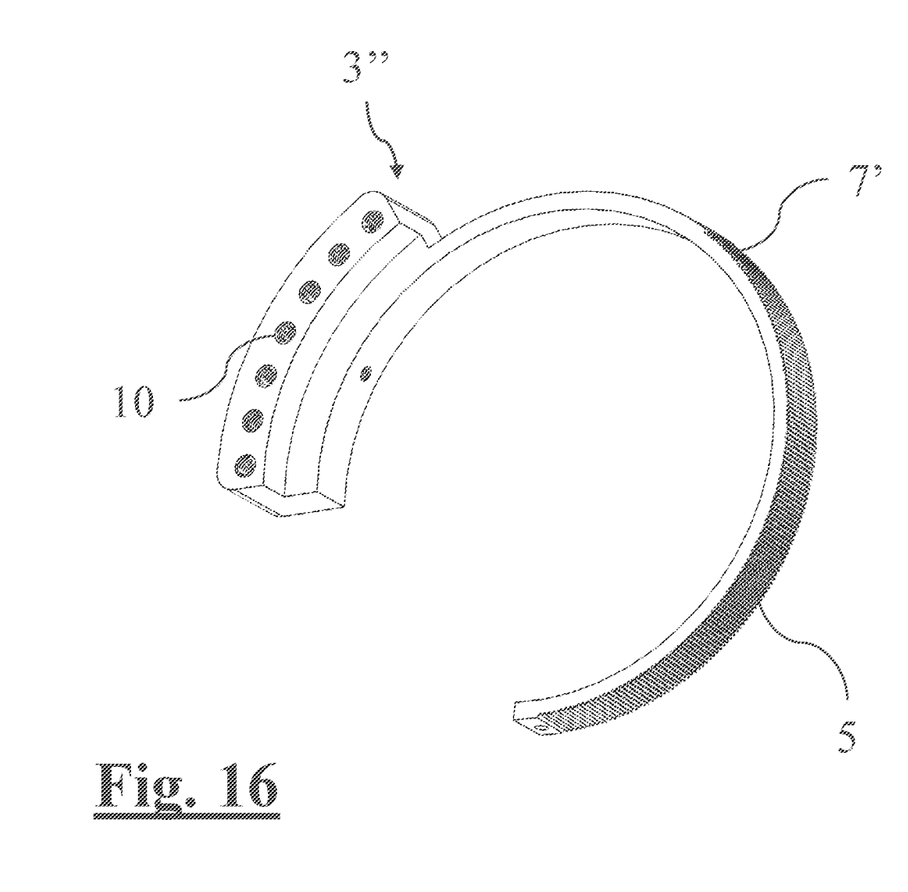
FIG. 16 shows a perspective view of a second element—referred to below as "second fixator body"—of the device according to FIG. 13.
Figure 17:
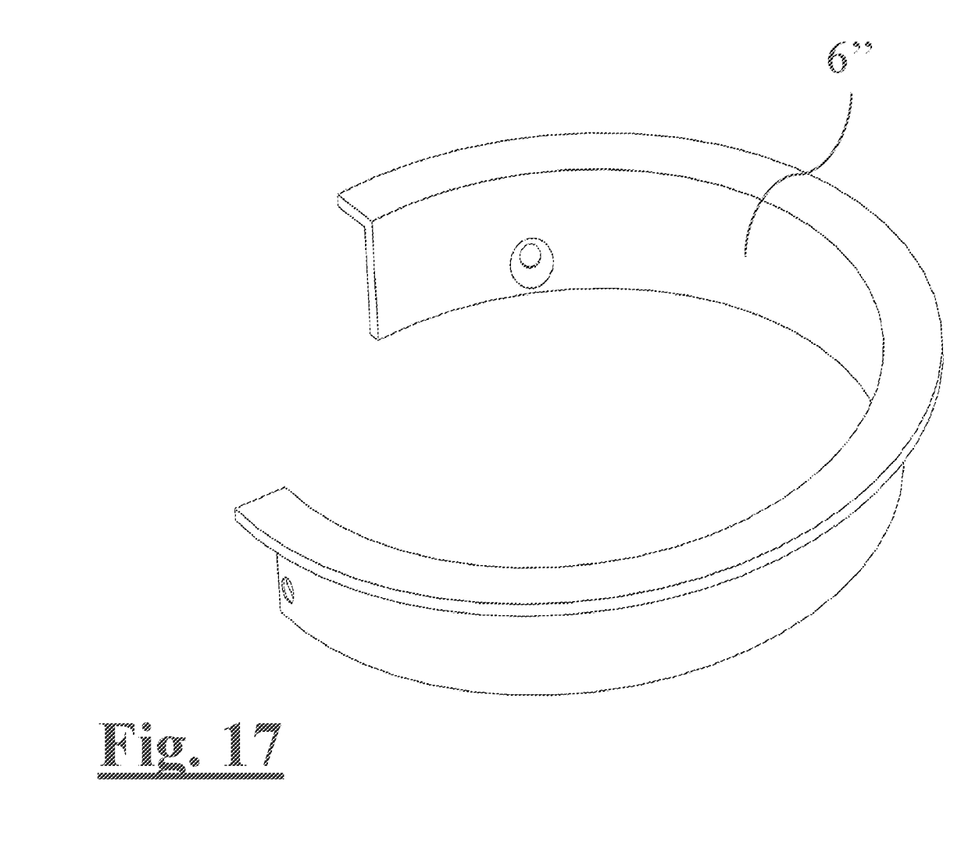
FIG. 17 shows a perspective view of a third element—referred to below as "flange"—of the device according to FIG. 13.

With reference to the attached FIGS. 1 and 2, 1 denotes a first embodiment of a device for the angular correction of a lower limb in pediatric patients according to the present invention.

The device comprises a first fixator body 2 and a second fixator body 3, both ring-shaped and coupled together rotatably along an axis of rotation perpendicular to the plane of lie of said bodies.

The first fixator body 2 comprises two annular guide pieces 8, which are parallel to each other, and an enlarged lateral base 9 at the top provided with three holes. Screws are inserted into the holes and allow the element to be associated with fixator rings 100 and/or screw connectors 101 and ultimately allow the fixator body 2 to be coupled to the patient's bone.

The second fixator body 3 comprises on the other hand a collar 7 which is defined by a thin cylindrical wall and is introduced between the two aforementioned guide pieces 8. The second fixator body 3 also has, in an outer lateral position, a base 10 with seven holes for coupling with rings 100 and/or screw connectors 101.

The relative locking together of the two fixator bodies 2, 3 is performed by means of a flange 6 which is defined by a circular metal plate and is coupled to the inner surface of the collar 7 by means of fixing screws. The flange 6 has a height greater than the height of the collar 7 and defines a radial abutment for the two guide pieces 8, preventing relative displacement—apart from rotation—of the two fixator bodies 2, 3.

The device 1 has means for the angular precision adjustment of the relative position of the two fixator bodies 2, 3.

These means comprise a toothing 5 formed along a section of the outer surface of the collar 7, and an operating member 4, in this case a worm screw rotatably mounted inside the base 9 of the first fixator body 2.

The worm screw comprises two opposite hexagonal-socket heads 11 which emerge from the base 9 and which may be operated, by means of engagement with the toothing 5, so as to vary the relative position of the two fixator bodies 2, 3.

With reference to the attached FIGS. 3 to 12, 1' denotes a second embodiment of the device for the angular correction of a lower limb.

This form corresponds substantially to the form described above, except that, for ergonomic reasons, the first and second fixator bodies 2', 3' are configured as a ring portion, namely as arcs of a circumference which subtend an angle of between about 235° and 305°.

The aforementioned description applies, mutatis mutandis, to this second embodiment; the figures show elements and portions of elements which are identical using the same reference number with the addition, where necessary, of a prime symbol where its shape has been modified to adapt to the new configuration.

With reference to the attached FIGS. 13 to 17, 1" denotes a third embodiment of the device for the angular correction of a lower limb.

This third embodiment corresponds essentially to the second embodiment described above, excepts for the aspects which are discussed below.

As regards the other aspects, the aforementioned description applies, mutatis mutandis, to this third embodiment; the figures show elements and portions of elements which are the same using the same reference number with the addition, where necessary, of a double prime symbol where its shape has been modified with respect to the previous embodiment.

Differently from the second embodiment, the third variant has a single guide piece 8" placed over the collar 7' of the second fixator body 3". In order to constrain the elements in the axial direction, the flange 6" therefore has a 90° flap at its top end which abuts above the guide piece 8", constraining it axially to the collar 7'.

A first advantage of the device according to the present invention is that its implant does not require osteotomy, making the treatment for angular correction of the lower limb less painful for the patient.

Another advantage of the device is that it is able to perform gradual corrections of the defect, while respecting the cartilage growth of the patient.

A further advantage is associated with the possibility of controlling the correction during application thereof, ensuring that the expected position is reached.

Yet another advantage consists in the reduction of the application and treatment times compared to the systems of the prior art.

Yet another advantage lies in the possibility of out-patient removal of the device.

Obviously, the person skilled in the art may make numerous modifications and variations to the invention described above in order to satisfy any specific requirements which might arise, all of these being however contained within the scope of protection of the invention as defined by the following claims.

What is claimed is:

1. A device for the angular correction of a lower limb in pediatric patients, comprising:

a first fixator body and a second fixator body which are both shaped like a ring or ring portion and can be placed around a lower limb and fixed to a first and second bone sites of said lower limb straddling a growth cartilage, said first fixator body and said second fixator body being constrained together slidably along their annular extension, wherein the first fixator body and the second fixator body respectively comprise a first attachment base and a second attachment base;

an adjusting mechanism suitable for allowing the relative sliding of said first fixator body with respect to said second fixator body, wherein said adjusting mechanism comprises an operating member constrained to said first fixator body, said operating member engaging with a toothing integral with said second fixator body, wherein said toothing is formed externally on a cylindrical collar of said second fixator body; and first fixation elements, for fixing the first fixator body to the first bone site;

second fixation elements, for fixing the second fixator body to the second bone site, wherein said first fixation elements are directly at the first attachment base;

wherein said second fixation elements are directly at the second attachment base;

the first fixator body, second fixator body, adjusting mechanism, first fixation elements and second fixation elements are comprised in a ring assembly or ring portion assembly of the device;

said device comprising only a single ring assembly or ring portion assembly;

wherein said first fixator body comprises at least one circular-shaped guide piece, said guide piece being slidably constrained to the collar by a flange which is coupled to said collar, and wherein the first and the second bone sites are both in the vicinity of the growth cartilage of the lower limb.

2. The device according to claim 1, wherein said operating member is a worm screw extending in a tangential direction with respect to said collar of the second fixator body.

3. The device according to claim 1, wherein said at least one guide piece is placed over said collar along a relative rotation axis of the two fixator bodies; said flange being a cylindrical plate which is coupled internally to the collar and which radially contains the at least one guide piece.

4. The device according to claim 1, wherein said flange is coupled to said collar by means of fastening screws or other reversible fastening system.

5. The device according to claim 1, wherein the guide pieces are two in number, are planar-shaped and parallel to each other, said collar being inserted between said guide pieces.

6. The device according to claim 1, wherein said guide piece is one in number and said flange comprises a horizontal flap which surrounds and contains said guide piece.

7. The device according to claim 1, wherein the first fixation elements and the second fixation elements are a fixator ring or half-ring and/or screw connectors.

* * * * *